United States Patent
Li et al.

(10) Patent No.: US 11,717,227 B2
(45) Date of Patent: Aug. 8, 2023

(54) SIGNAL PROCESSING DEVICE AND SIGNAL PROCESSING METHOD

(71) Applicant: Tsinghua University, Beijing (CN)

(72) Inventors: Xinyi Li, Beijing (CN); Huaqiang Wu, Beijing (CN); He Qian, Beijing (CN); Bin Gao, Beijing (CN)

(73) Assignee: Tsinghua University, Beijing (CN)

( * ) Notice: Subject to any disclaimer, the term of this patent is extended or adjusted under 35 U.S.C. 154(b) by 548 days.

(21) Appl. No.: 16/751,110

(22) Filed: Jan. 23, 2020

(65) Prior Publication Data
US 2020/0237311 A1 Jul. 30, 2020

(30) Foreign Application Priority Data
Jan. 28, 2019 (CN) .......................... 201910081039.3

(51) Int. Cl.
| | |
|---|---|
| *G11C 13/00* | (2006.01) |
| *A61B 5/00* | (2006.01) |
| *A61B 5/316* | (2021.01) |
| *A61B 5/374* | (2021.01) |
| *A61B 5/389* | (2021.01) |

(52) U.S. Cl.
CPC ............ *A61B 5/7207* (2013.01); *A61B 5/316* (2021.01); *A61B 5/374* (2021.01); *A61B 5/389* (2021.01); *G11C 13/0026* (2013.01); *G11C 13/0028* (2013.01); *G11C 2213/77* (2013.01)

(58) Field of Classification Search
CPC ....... A61B 5/7207; A61B 5/316; A61B 5/374; A61B 5/389; G11C 13/0026; G11C 13/0028; G11C 2213/77; G11C 7/1006; G11C 11/54; G11C 13/0002;
(Continued)

(56) References Cited

U.S. PATENT DOCUMENTS

| | | | | |
|---|---|---|---|---|
| 2019/0147330 A1* | 5/2019 | Otsuka | .................... | G11C 11/54 706/29 |
| 2021/0174173 A1* | 6/2021 | Li | .......................... | G06N 3/049 |

(Continued)

FOREIGN PATENT DOCUMENTS

| | | |
|---|---|---|
| CN | 105160401 A | 12/2015 |
| CN | 107273972 A | 10/2017 |
| CN | 107424647 A | 12/2017 |

OTHER PUBLICATIONS

Face classification using electronic synapses. Peng Yao et al., Published May 12, 2017.
(Continued)

*Primary Examiner* — Khamdan N. Alrobaie
(74) *Attorney, Agent, or Firm* — Loeb & Loeb LLP (57) ABSTRACT

A signal processing device and a signal processing method. The signal processing device includes a receiver, a memristor array and a classifier. The receiver is configured to receive a first signal. The memristor array includes a plurality of memristor units, each of the plurality of memristor units includes a memristor, and the memristor array is configured to apply the first signal that has been received to at least one memristor unit of the plurality of memristor units and output a second signal based on a memristor resistance value distribution of the memristor array. The classifier is configured to classify the second signal outputted from the memristor array to obtain a type of the first signal.

20 Claims, 6 Drawing Sheets

(58) Field of Classification Search
CPC ............ G11C 2213/79; G11C 2213/82; G06N 3/0445; G06N 3/0454; G06N 3/0675; G06N 3/084
See application file for complete search history.

(56) References Cited

U.S. PATENT DOCUMENTS

2022/0047200 A1* 2/2022 Wu ................ G06N 3/0635
2022/0061729 A1* 3/2022 Wu ................ G11C 13/003

OTHER PUBLICATIONS

Electronic system with memristive synapses for pattern recognition. Sangsu Park et al., Published May 5, 2015.

* cited by examiner

SIGNAL PROCESSING DEVICE AND SIGNAL PROCESSING METHOD

The present application claims priority of the Chinese Patent Application No. 201910081039.3, filed on Jan. 28, 2019 and entitled "Signal Processing Device and Signal Processing Method", the disclosure of which is incorporated herein by reference in its entirety as part of the present application.

TECHNICAL FIELD

Embodiments of the present disclosure relate to a signal processing device and a signal processing method.

BACKGROUND

Non-stationary random signals refer to signals whose distribution parameters or distribution laws vary with time. At present, the research on analysis and processing of the non-stationary random signals has attracted widespread attention and has been increasingly developed.

Electroencephalogram signals are electrical pulse signals generated by a human brain, which are relatively common non-stationary random signals. The electroencephalogram signals contain information about emotions, thinking activities, or nervous system diseases of a human. Analysis and decoding of the electroencephalogram signals are widely used in fields such as brain-computer interface (BCI) and medical treatment.

At present, a common electroencephalogram signal processing method is to decode an electroencephalogram signal by using a digital signal processing method such as Fourier transform and wavelet transform, etc., in a computer or a digital signal processor, after anti-aliasing filtering and analog-digital signal conversion. In other words, the current electroencephalogram signal decoding is implemented by software. However, an electroencephalogram signal processing system based on a software decoding method requires the support of a hardware system with a large volume and high power consumption.

SUMMARY

At least one embodiment of the present disclosure provides a signal processing device. The signal processing device includes a receiver, a memristor array and a classifier. The receiver is configured to receive a first signal; the memristor array comprises a plurality of memristor units, each of the plurality of memristor units comprises a memristor, and the memristor array is configured to apply the first signal that has been received to at least one memristor unit in the plurality of memristor units and output a second signal based on a memristor resistance value distribution of the memristor array; and the classifier is configured to classify the second signal outputted from the memristor array to obtain a type of the first signal.

For example, in the signal processing device according to some embodiments of the present disclosure, the memristor array further includes a plurality of word lines, a plurality of bit lines and a plurality of source lines; and each of the plurality of memristor units is correspondingly connected with one word line in the plurality of word lines, one bit line in the plurality of bit lines, and one source line in the plurality of source lines, respectively.

For example, in the signal processing device according to some embodiments of the present disclosure, the memristor array is configured to: apply the first signal to at least one memristor unit in the plurality of memristor units through at least one bit line in the plurality of bit lines, and output the second signal through at least one source line in the plurality of source lines; or apply the first signal to at least one memristor unit in the plurality of memristor units through at least one source line in the plurality of source lines, and output the second signal through at least one bit line in the plurality of bit lines.

For example, in the signal processing device according to some embodiments of the present disclosure, the memristor array is further configured to segment the first signal that has been received to form signal segments, and apply respective signal segments to corresponding memristor units in the plurality of memristor units.

For example, in the signal processing device according to some embodiments of the present disclosure, the memristor array is configured to receive a switch control signal through at least one word line in the plurality of word lines, and select a memristor unit to be applied with the first signal based on the switch control signal.

For example, in the signal processing device according to some embodiments of the present disclosure, each of the plurality of memristor units further includes a transistor connected in series with the memristor in each of the plurality of memristor units.

For example, in the signal processing device according to some embodiments of the present disclosure, the memristor in each of the plurality of memristor units is a continuously adjustable multi-resistance state memristor.

For example, the signal processing device according to some embodiments of the present disclosure further includes a pre-processing circuit, wherein the pre-processing circuit is configured to pre-process the first signal received by the receiver, so as to form a pre-processed signal having an amplitude within a predetermined range.

For example, in the signal processing device according to some embodiments of the present disclosure, the pre-processing circuit includes at least one of an amplifying circuit and a level shift circuit.

For example, in the signal processing device according to some embodiments of the present disclosure, the predetermined range is a resistive voltage interval of the memristor or a read voltage interval of the memristor.

For example, in the signal processing device according to some embodiments of the present disclosure, the first signal received by the receiver is an electroencephalogram signal.

At least one embodiment of the present disclosure further provides a signal processing method. The signal processing method includes: receiving, by a receiver, a first signal; applying, by a memristor array, the first signal that has been received to at least one memristor unit in a plurality of memristor units of the memristor array, and outputting, by the memristor array, a second signal based on a memristor resistance value distribution of the memristor array, wherein the memristor unit includes a memristor; and classifying, by a classifier, the second signal outputted from the memristor array to obtain a type of the first signal.

For example, in the signal processing method according to some embodiments of the present disclosure, the memristor array further includes a plurality of word lines, a plurality of bit lines and a plurality of source lines; the applying, by the memristor array, the first signal that has been received to at least one memristor unit in the plurality of memristor units of the memristor array, includes: applying the first signal to at least one memristor unit in the plurality of memristor units through at least one bit line in the plurality of bit lines; and the outputting, by the memristor array, the second signal based on the memristor resistance value distribution of the memristor array, includes: outputting the second signal through at least one source line in the plurality of source lines.

For example, in the signal processing method according to some embodiments of the present disclosure, the memristor array further includes a plurality of word lines, a plurality of bit lines and a plurality of source lines; the applying, by the memristor array, the first signal that has been received to at least one memristor unit in the plurality of memristor units of the memristor array, includes: applying the first signal to at least one memristor unit in the plurality of memristor units through at least one source line in the plurality of source lines; and the outputting, by the memristor array, the second signal based on the memristor resistance value distribution of the memristor array, includes: outputting the second signal through at least one bit line in the plurality of bit lines.

For example, in the signal processing method according to some embodiments of the present disclosure, the applying, by the memristor array, the first signal that has been received to at least one memristor unit in the plurality of memristor units of the memristor array, includes: segmenting the first signal that has been received to form signal segments, and applying respective signal segments to corresponding memristor units in the plurality of memristor units.

For example, in the signal processing method according to some embodiments of the present disclosure, the memristor array further includes a plurality of word lines, a plurality of bit lines and a plurality of source lines, and the applying, by the memristor array, the first signal that has been received to at least one memristor unit in the plurality of memristor units of the memristor array, includes: receiving a switch control signal through at least one word line in the plurality of word lines, and selecting a memristor unit to be applied with the first signal based on the switch control signal.

For example, the signal processing method according to some embodiments of the present disclosure further includes: pre-processing, by a pre-processing circuit, the first signal that has been received, so as to form a pre-processed signal having an amplitude within a predetermined range.

For example, in the signal processing method according to some embodiments of the present disclosure, the pre-processing includes at least one selected from the group consisting of amplifying the first signal that has been received and level shifting the first signal that has been received.

For example, in the signal processing method according to some embodiments of the present disclosure, the predetermined range is a resistive voltage interval of the memristor or a read voltage interval of the memristor.

For example, the signal processing method according to some embodiments of the present disclosure, before the applying, by the memristor array, the first signal that has been received to at least one memristor unit in the plurality of memristor units of the memristor array, further includes: initializing the memristor array, so that initial states of respective memristors in the memristor array are substantially the same.

BRIEF DESCRIPTION OF THE DRAWINGS

In order to clearly illustrate the technical solutions of the embodiments of the disclosure, the drawings of the embodiments will be briefly described in the following; it is obvious that the described drawings are only related to some embodiments of the disclosure and thus are not limitative to the disclosure.

DETAILED DESCRIPTION

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

The terms used herein to describe embodiments of the present application are not intended to restrict and/or limit the scope of the present disclosure.

For example, unless otherwise defined, all the technical and scientific terms used herein have the same meanings as commonly understood by one of ordinary skill in the art to which the present disclosure belongs.

It should be understood that the terms "first," "second," etc., which are used in the present disclosure, are not intended to indicate any sequence, amount or importance, but distinguish various components. Unless clearly otherwise indicated in the context, the terms "a," "an" or "the," etc., are not intended to indicate a limitation of quantity, but rather indicate the presence of at least one.

In should be further understood that, the terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

Hereinafter, exemplary embodiments of the present disclosure will be described in detail with reference to the accompanying drawings. In the accompanying drawings, the same reference numerals or numbers may refer to components or elements that perform substantially the same function.

At least one exemplary embodiment of the present disclosure provides a signal processing device. The signal processing device includes a receiver, a memristor array and a classifier, wherein the receiver is configured to receive a first signal; the memristor array includes a plurality of memristor units, each of the plurality of memristor units includes a memristor, and the memristor array is configured to apply the first signal that has been received to at least one memristor unit in the plurality of memristor units and output a second signal based on a memristor resistance value distribution of the memristor array; and the classifier is configured to classify the second signal outputted from the memristor array to obtain a type of the first signal.

At least one exemplary embodiment of the present disclosure provides a signal processing method. The signal processing method includes: receiving, by a receiver, a first signal; applying, by a memristor array, the first signal that has been received to at least one memristor unit in a plurality of memristor units of the memristor array, and outputting, by the memristor array, a second signal based on a memristor resistance value distribution of the memristor array, wherein the memristor unit includes a memristor; and classifying, by a classifier, the second signal outputted from the memristor array to obtain a type of the first signal.

A memristor is a passive electronic device; and electrical pulse excitations with different amplitudes/frequencies will cause redistribution of ions in the memristor, which will be further presented as different resistance values. For example, the resistance value of the memristor may vary with a voltage or a current applied.

Figure 1:
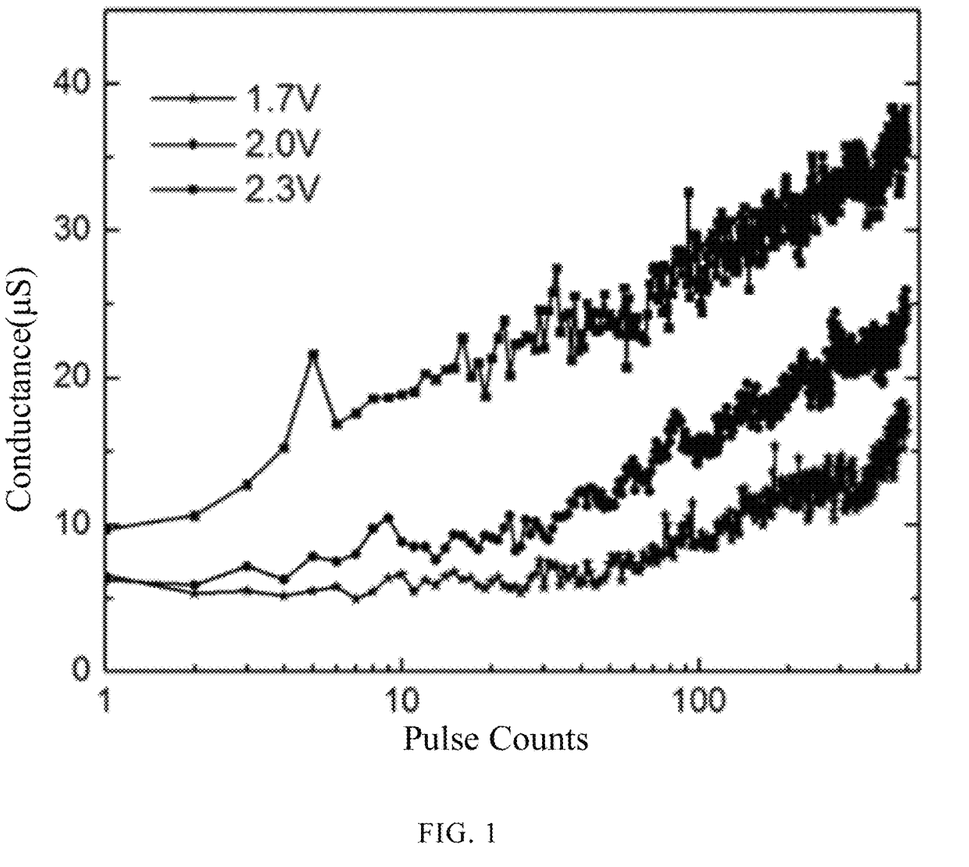
FIG. 1 is a schematic diagram of a device characteristic of a memristor according to an exemplary embodiment of the present disclosure.

FIG. 1 is a schematic diagram of a device characteristic of a memristor according to an exemplary embodiment of the present disclosure.

Referring to FIG. 1, electrical pulses with amplitudes of 1.7 volts (V), 2.0 V and 2.3 V are applied to the memristor, respectively, and pulse widths of the respective electrical pulses are all 10 nanoseconds (ns), so that characteristic curves under different amplitudes can be obtained, where a connection line of star-shaped dots indicates a characteristic curve obtained by applying the voltage of 1.7 V, a connection line of round dots indicates a characteristic curve obtained by applying a voltage of 2.0 V, and a connection line of square dots indicates a characteristic curve obtained by applying a voltage of 2.3 V. It can be seen from FIG. 1 that, when the amplitude of the voltage applied to the memristor is relatively small, the variation amplitude of the resistance value of the memristor is relatively small; and when the amplitude of the voltage applied to the memristor is relatively large, the variation amplitude of the resistance value of the memristor is relatively large. Due to such characteristic, the memristor can be applied to a signal processing device or a signal processing method for identifying different types of signals.

Figure 2:
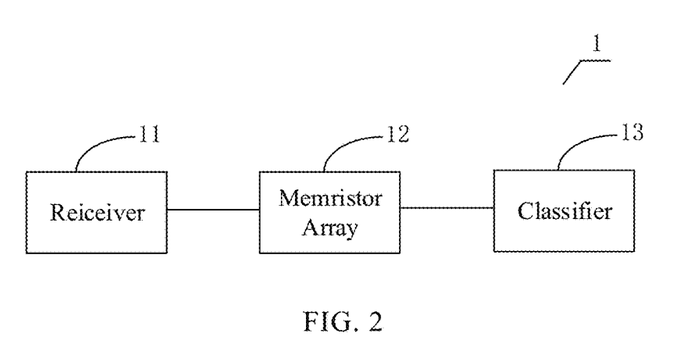
FIG. 2 is a schematic structural diagram of a signal processing device according to an exemplary embodiment of the present disclosure.

FIG. 2 is a schematic structural diagram of a signal processing device according to an exemplary embodiment of the present disclosure.

Referring to FIG. 2, the signal processing device 1 according to the exemplary embodiment of the present disclosure can include a receiver 11, a memristor array 12 and a classifier 13.

In the signal processing device 1, the receiver 11 can be configured to receive a first signal, wherein the first signal is a signal to be identified. For example, the first signal can be a non-stationary random signal. For example, the non-stationary random signal can be an electroencephalogram signal. For example, the number of the first signals can be one or more. That is to say, the signal processing device 1 according to the exemplary embodiment of the present disclosure can identify one first signal or a plurality of first signals to obtain a type(s) of the first signal(s).

In the signal processing device 1, the memristor array 12 can be configured to apply the first signal that has been received to at least one memristor unit in a plurality of memristor units of the memristor array, and output a second signal based on a memristor resistance value distribution of the memristor array. Thus, the memristor array 12 can encode the first signal into the second signal based on the memristor resistance value distribution of the memristor array 12. Because the memristor is small in volume, low in power consumption and easy to be integrated with high density, the signal processing device 1 according to the embodiment of the present disclosure has advantages of small volume, low power consumption and easy integration. In addition, because the memristor array 12 converts the first signal into the second signal, no additional analog-to-digital conversion component is required to process the first signal, and the second signal obtained can be used for classification; and therefore, the signal processing device 1 according to the embodiment of the present disclosure further reduces the volume and cost.

In the signal processing device 1, the classifier 13 can be configured to classify the second signal outputted by the memristor array, to obtain the type of the first signal.

For example, the classifier 13 can include a neural network classifier. For example, the classifier 13 can be further configured to classify the second signal outputted from the memristor array by using a neural network classification method, to obtain the type of the first signal. For example, the neural network classification method can include a back propagation (BP) neural network method, a radial basis function (RBF) neural network method, a convolutional neural network method, etc. Because the second signal is based on the memristor resistance value distribution of the memristor array 12, the second signal can be easily classified and identified by the classifier. Further, by classifying and identifying the second signal, the type of the first signal can be obtained.

For example, the classifier 13 can be implemented by at least one selected from the group consisting of an application specific integrated circuit (ASIC), a field programmable gate array (FPGA) and a graphics processing unit (GPU); or the classifier 13 can be implemented by hardware, firmware or software, as well as any combination thereof. In addition, these classifiers are trained with a large number of training sample sets, and these training sample sets include historical data obtained with respect to different situations. After being trained to a certain degree, the classifier can classify a new second signal being inputted.

Figure 3:
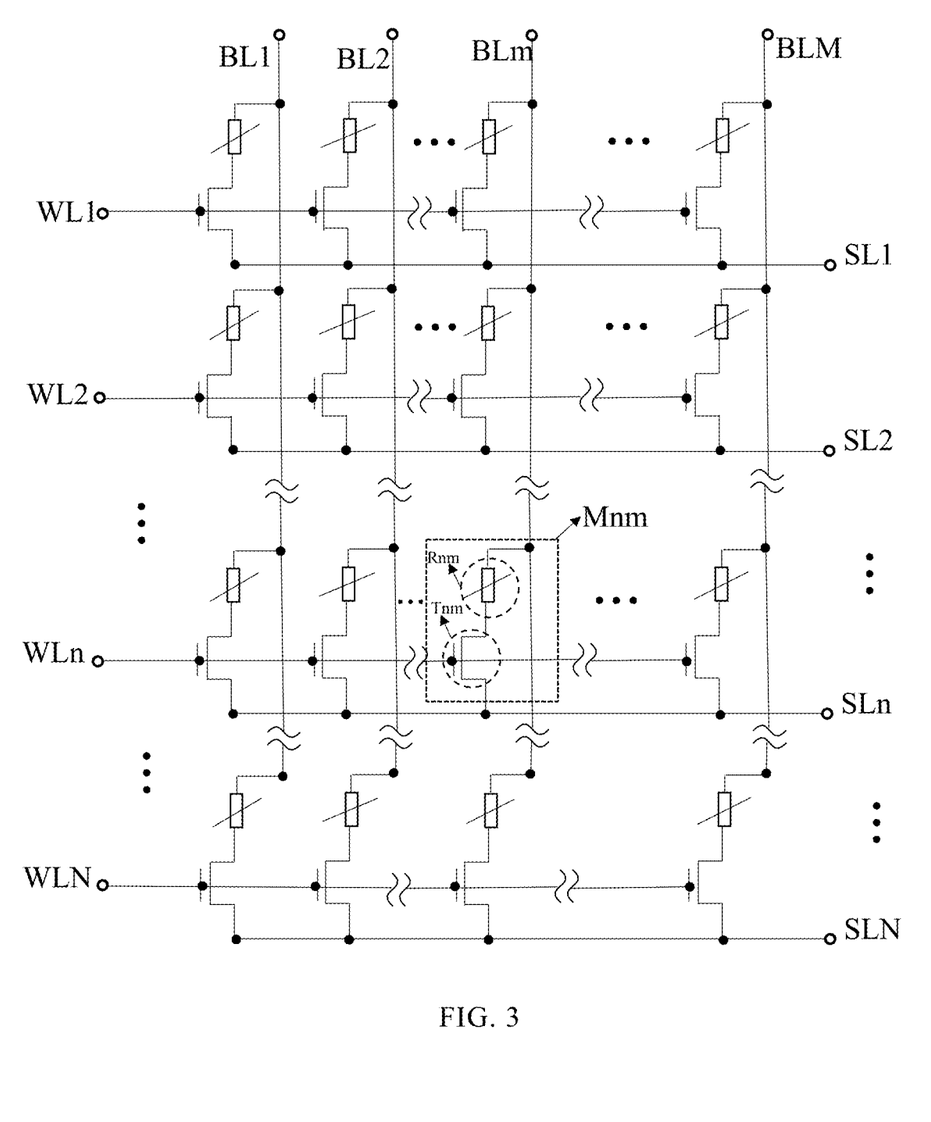
FIG. 3 is a schematic structural diagram of a memristor array according to an exemplary embodiment of the present disclosure.

FIG. 3 is a schematic structural diagram of the memristor array according to an exemplary embodiment of the present disclosure.

Referring to FIG. 3, the memristor array 12 according to the exemplary embodiment of the present disclosure can be an N*M memristor array, where N and M are both integers greater than or equal to 1. For example, N and M are both integers greater than or equal to 10, or integers greater than or equal to 100. As shown in FIG. 3, the memristor array 12 can include N word lines from a word line WL1 to a word line WLN, M bit lines from a bit line BL1 to a bit line BLM, N source lines from a source line SL1 to a source line SLN, and N*M memristor units. For example, each memristor unit in the N*M memristor units can include a transistor (T) and a memristor (R), that is, a 1T1R structure, but the embodiment of the present disclosure is not limited thereto. For example, the memristor included in each memristor unit is a continuously adjustable multi-resistance state memristor. Taking the mth memristor unit Mnm in the nth row as an example, where n is an integer greater than or equal to 1 and less than or equal to N, the memristor unit Mnm can include a transistor Tnm and a memristor Rnm. For example, the transistor Tnm can be a MOS transistor. For example, a gate electrode of the transistor Tnm is connected with a word line WLn, a source electrode of the transistor Tnm is connected with a source line WLn, a drain electrode of the transistor Tnm is connected with one end of the memristor Rnm, and the other end of the memristor Rnm is connected with a bit line BLn. Connections of the other memristor units with the word lines, the bit lines and the source lines are similar to that of the memristor unit Mnm, and details will not be repeated here.

For example, the memristor array 12 can be configured to: apply the first signal to a corresponding memristor unit through at least one bit line in the bit lines BL1 to BLM; and output a second signal through at least one source line in the source lines SL1 to SLN. For example, when the number of first signals that have been received is one, one bit line can be selected from the bit lines BL1 to BLM to apply the first signal to the corresponding memristor unit therethrough, and one source line can be selected from the source lines SL1 to SLN to output a second signal. For example, when the number of first signals that have been received is three, three bit lines can be selected from the bit lines BL1 to BLM to receive the three first signals, respectively, and corresponding source lines can be selected from the source lines SL1 to SLN to output second signals.

The embodiment in which the memristor array 12 is configured to receive a first signal through a bit line and output a second signal through a source line is described above, but the present disclosure is not limited thereto. For example, as another example, the memristor array 12 can be configured to receive a first signal through a source line and output a second signal through a bit line. For example, the memristor array 12 can be configured to: apply the first signal to a corresponding memristor unit through at least one source line in the source lines SL1 to SLN; and output the second signal through at least one bit line in the bit lines BL1 to BLM. For example, when the number of first signals that have been received is one, one source line can be selected from the source lines SL1 to SLN to receive the first signal, and a corresponding bit line can be selected from the bit lines BL1 to BLM to output the second signal. For example, when the number of first signals that have been received is three, three source lines can be selected from the source lines SL1 to SLN to receive the three first signals, respectively, and corresponding bit lines can be selected from the bit lines BL1 to BLM to output second signals.

For example, the memristor array 12 can be further configured to segment the first signal that has been received to form signal segments, and apply respective signal segments to memristor units that correspond to source lines receiving the first signal among the N*M memristor units, for example, different memristor units correspond to different segments of the first signal. After each memristor unit receives a corresponding segment of the first signal, a resistance value of the memristor in the memristor unit is changed under an action of the corresponding signal segment of the first signal.

For example, the memristor array 12 can be further configured to receive a switch control signal through at least one word line in the word lines WL1 to WLN, and select a memristor unit to be applied with the first signal based on the switch control signal. For example, the switch control signal can include a set signal or a reset signal, for selecting a corresponding memristor or not selecting a corresponding memristor.

For example, the signal processing device 1 can further include a word line decoder (not shown) connected with the word lines WL1 to WLN of the memristor array, and the word line decoder can be configured to receive the switch control signal and send the same to at least one word line in the word lines WL1 to WLN.

Figure 4:
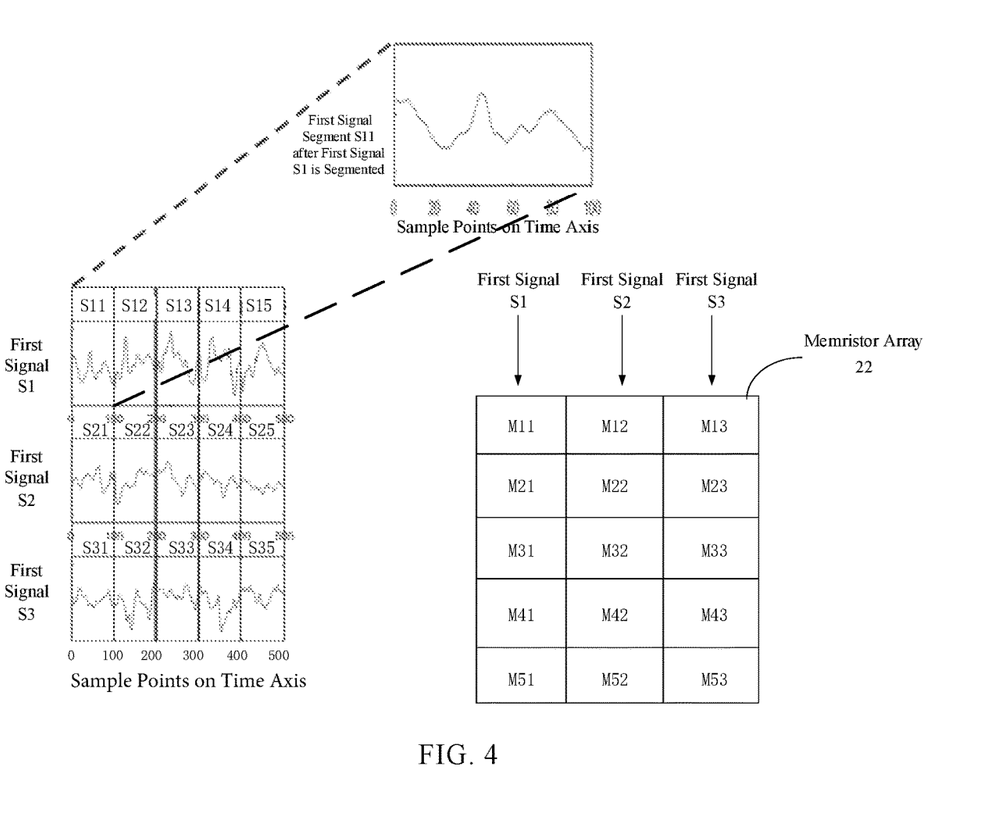
FIG. 4 is a mapping diagram of applying respective first signals through bit lines to corresponding memristor units of a memristor array in a case where the number of first signals that have been received is three, according to an exemplary embodiment of the present disclosure.

FIG. 4 is a mapping diagram of applying respective first signals through bit lines to corresponding memristor units of a memristor array 22 in a case where the number of first signals that have been received is three, according to an exemplary embodiment of the present disclosure.

Referring to FIG. 4, the first signals received by the receiver include a first signal S1, a first signal S2 and a first signal S3, wherein time domain diagrams of the first signal S1, the first signal S2 and the first signal S3 are different from each other. By configuring the switch control signal, 15 memristor units M11 to M51, M12 to M52, M13 to M53 can be selected from the memristor array 22 as the memristor units to which the first signals are applied. The memristor array 22 can be configured to apply, through the bit line BL1, the first signal S1 to the memristor units corresponding to the bit line BL1, apply, through the bit line BL2, the first signal S2 to the memristor units corresponding to the bit line BL2, and apply, through the bit line BL3, the third signal S3 to the memristor units corresponding to the bit line BL3.

Referring to FIG. 4, for example, the memristor array 22 can be further configured to: segment the first signal S1 to form five signal segments S11 to S15, and apply the five signal segments S11 to S15 to the memristor units M11 to M51 in the memristor array 22, respectively; segment the first signal S2 to form five signal segments S21 to S25, and apply the five signal segments S21 to S25 to the memristor units M12 to M52, respectively; segment the first signal S3 to form five signal segments S31 to S35, and apply the five signal segments S31 to S35 to the memristor units M13 to M53. Thus, the memristor array 22 can encode the first signal S1, the first signal S2 and the first signal S3 into second signals based on the memristor resistance value distribution of the memristor array 22. In addition, the memristor array 22 can further be configured to output the second signals through source lines SL1 to SL5.

Figure 5:
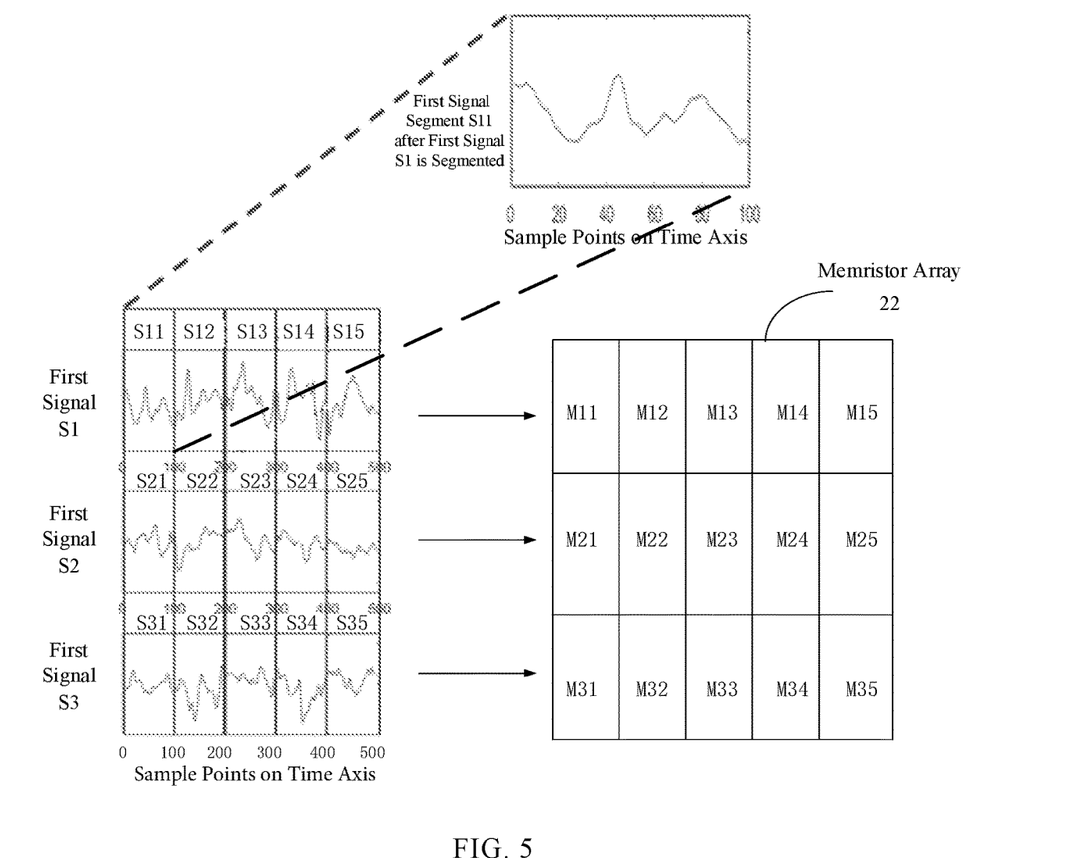
FIG. 5 is a mapping diagram of applying respective first signals through source lines to corresponding memristor units of a memristor array in a case where the number of first signals that have been received is three, according to an exemplary embodiment of the present disclosure.

FIG. 5 is a mapping diagram of applying respective first signals through source lines to corresponding memristor units of a memristor array in a case where the number of first signals that have been received is three, according to an exemplary embodiment of the present disclosure.

Referring to FIG. 5, the first signals received by the receiver include a first signal S1, a first signal S2 and a first signal S3, wherein time domain diagrams of the first signal S1, the first signal S2 and the first signal S3 are different from each other. By configuring the switch control signal, 15 memristor units M11 to M15, M21 to M25, M31 to M35 can be selected from the memristor array 22 as the memristor units to which the first signals are applied. The memristor array 22 can be configured to: apply, through the source line SL1, the first signal S1 to the memristor units corresponding to the source line SL1, apply, through the source line SL2, the first signal S2 to the memristor units corresponding to the source line SL2, and apply, through the source line SL3, the first signal S3 to the memristor units corresponding to the source line SL3.

Referring to FIG. 5, for example, the memristor array 22 can be further configured to: segment the first signal S1 to form five signal segments S11 to S15, and apply the five signal segments S11 to S15 to the memristor units M11 to M15 in the memristor array 22, respectively; segment the first signal S2 to form five signal segments S21 to S25, and apply the five signal segments S21 to S25 to the memristor units M21 to M25 in the memristor array 22, respectively; segment the first signal S3 to form five signal segments S31 to S35, and apply the five signal segments S31 to S35 to the memristor units M31 to M35 in the memristor array 22, respectively. Thus, the memristor array 22 can encode the first signal S1, the first signal S2 and the first signal S3 into second signals based on the memristor resistance value distribution of the memristor array 22. In addition, the memristor array 22 can further be configured to output the second signals through bit lines BL1 to BL5.

Figure 6A:
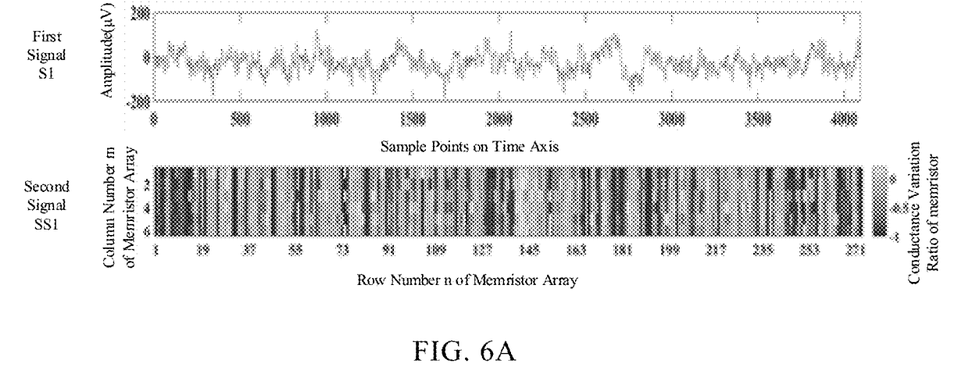
FIG. 6A to FIG. 6C show time domain diagrams of first signals, and schematic diagrams of second signals based on a memristor resistance distribution of a memristor array after the first signals are applied to the memristor array, according to an exemplary embodiment of the present disclosure.
Figure 6B:
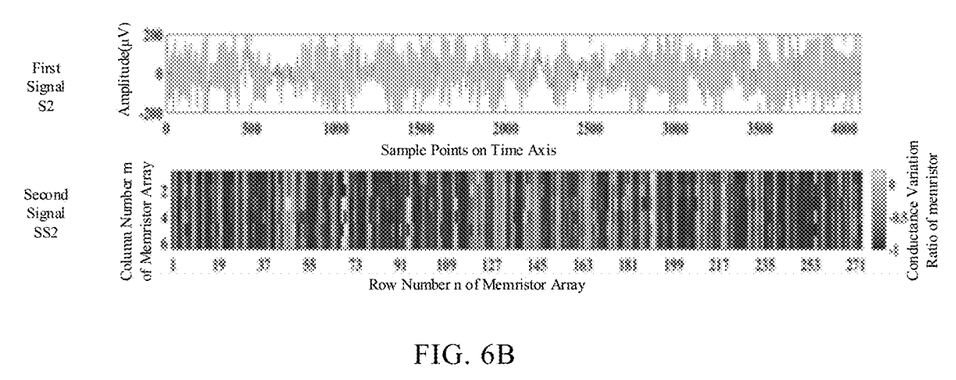
Figure 6C:
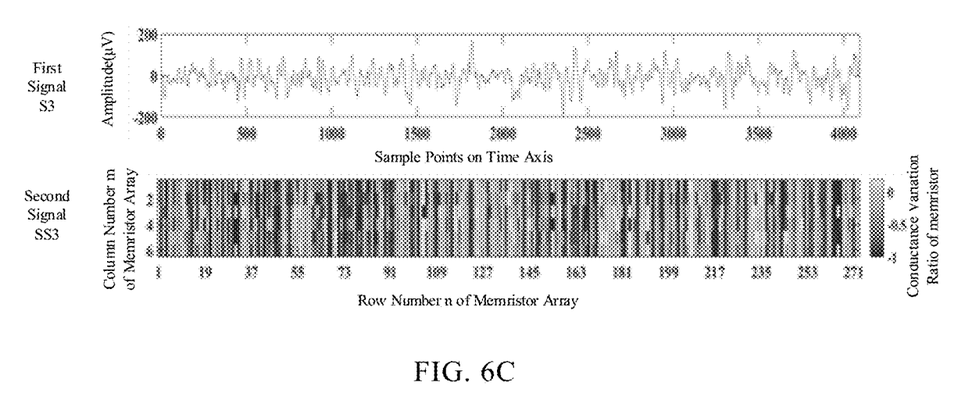

FIG. 6A to FIG. 6C are schematic diagrams of a first signal S1, a first signal S2 and a first signal S3, as well as a second signal SS1, a second signal SS2 and a second signal SS3 based on a memristor resistance distribution of a memristor array 22 after the first signal S1, the first signal S2 and the first signal S3 are applied to the memristor array 22. Specifically, FIG. 6A shows a time domain diagram of the first signal S1, and a schematic diagram of the second signal SS1 based on the memristor resistance distribution of the memristor array 22 after the first signal S1 is applied to the memristor array 22. FIG. 6B shows a time domain diagram of the first signal S2, and a schematic diagram of the second signal SS2 based on the memristor resistance distribution of the memristor array 22 after the first signal S2 is applied to the memristor array 22. FIG. 6C shows a time domain diagram of the first signal S3, and a schematic diagram of the second signal SS3 based on the memristor resistance distribution of the memristor array 22 after the first signal S3 is applied to the memristor array 22. With respect to the schematic diagrams of the second signals in FIG. 6A to FIG. 6C, a conductance variation ratio of a memristor is represented by different color shades, wherein the conductance variation ratio of the memristor refers to a ratio of a difference, between a conductance of the memristor after the first signal is applied and a conductance of the memristor before the first signal is applied, to the conductance of the memristor before the first signal is applied.

Referring to FIG. 6A to FIG. 6C, the first signal S1, the first signal S2 and the first signal S3 are all spike signals, but the time domain diagrams thereof are different from each other. Therefore, resistance distribution diagrams of the corresponding memristors in the memristor array 22 are also different from each other. That is to say, with respect to different first signals, different memristor resistance distributions of the memristor array can be obtained. As a result, the memristor array 22 can convert a spike signal into a second signal based on a memristor resistance distribution of the memristor array 22, so that a classifier 13 can classify the second signal based on the memristor resistance distribution of the memristor array 22, to obtain a type of the first signal.

For example, in FIG. 6A, the first signal S1 may be an electroencephalogram signal when a healthy person opens his/her eyes, and the second signal SS1 may be based on a memristor resistance value distribution of the memristor array 22 after the first signal S1 is applied to the memristor array 22. In FIG. 6B, the first signal S2 may be an electroencephalogram signal when a healthy person closes his/her eyes, and the second signal SS2 may be based on a memristor resistance value distribution of the memristor array 22 after the first signal S2 is applied to the memristor array 22. In FIG. 6C, the first signal S3 may be an electroencephalogram signal outside a lesion region when an epileptic patient is not in epileptic seizure, and the second signal SS3 may be based on a memristor resistance value distribution of the memristor array 22 after the first signal S3 is applied to the memristor array 22. It can be seen from FIG. 6A to FIG. 6C that the second signal SS3 is significantly different from the second signal SS1 and the second signal SS2. Therefore, the signal processing device 1 according to the embodiment of the present disclosure can be used for identifying an electroencephalogram signal outside a lesion region when an epileptic patient is not in epileptic seizure.

Figure 7:
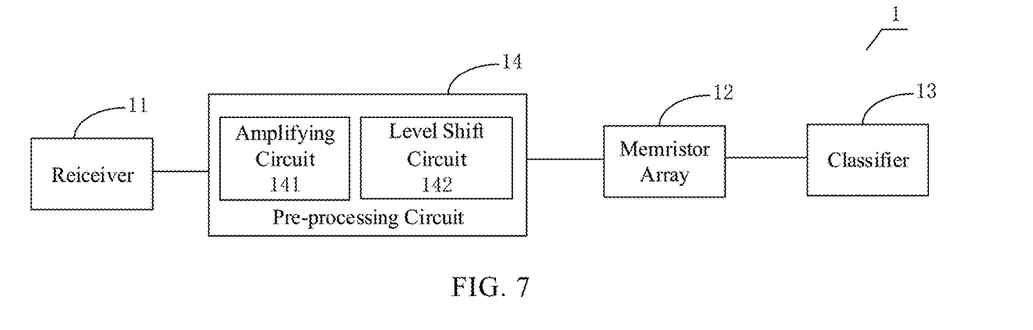
FIG. 7 is a schematic structural diagram of a signal processing device according to another exemplary embodiment of the present disclosure.

FIG. 7 is a schematic structural diagram of a signal processing device according to another exemplary embodiment of the present disclosure.

Referring to FIG. 7, in addition to the components shown in FIG. 2, the signal processing device according to the exemplary embodiment of the present disclosure can further include a pre-processing circuit 14. For example, the pre-processing circuit 14 can be configured to pre-process a first signal received by a receiver 11, so as to form a pre-processed signal having an amplitude within a predetermined range; and then send the pre-processed signal to a memristor array 12. For example, the predetermined range can be a resistive voltage interval of a memristor or a read voltage interval of a memristor. For example, a resistive voltage interval of a memristor may be 0.8 V to 2 V, and a read voltage interval of a memristor may be 0.1 V to 0.5 V.

Figure 8:
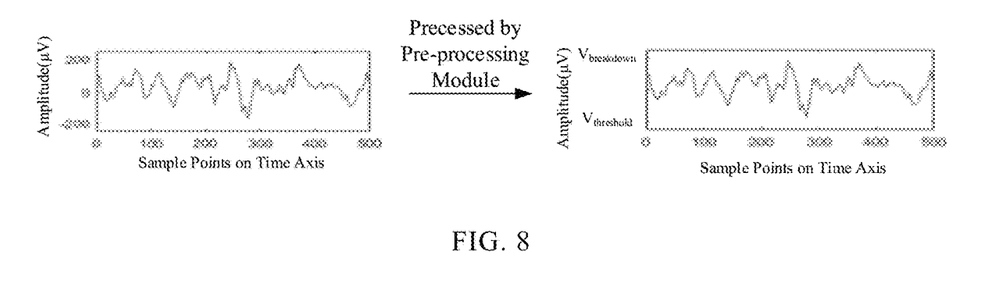
FIG. 8 is a schematic diagram of amplitude variation of a first signal after being processed by a pre-processing circuit according to an exemplary embodiment of the present disclosure.

For example, the pre-processing circuit 14 may include an amplifying circuit 141 and a level shift circuit 142. For example, the amplifying circuit 141 can be configured to amplify the first signal. For example, an amplification factor can be selected according to the amplitude of the first signal itself, for example, 1000. For example, the level shift circuit 142 can be configured to perform a level shift on the first signal being amplified so that the amplitude of the first signal is within the predetermined range. FIG. 8 is a schematic diagram of amplitude variation of the first signal after being processed by the pre-processing circuit. Referring to FIG. 8, the amplitude of the first signal after being amplified by the amplifying circuit 141 and shifted by the level shift circuit 142 is within a predetermined range from $V_{threshold}$ to $V_{breakdown}$ (e.g., $V_{breakdown}$ may be 2 V, and $V_{threshold}$ may be 0.8 V).

For example, the signal processing device can further comprise a signal acquisition circuit (not shown). The signal acquisition circuit can be configured to acquire the first signal and send the same to the receiver.

It should be noted that, the signal processing device according to the embodiments of the present disclosure as described above is merely an exemplary structure. However, the present disclosure is not limited thereto. For example, some components therein may be omitted or additional components may be added.

Figure 9:
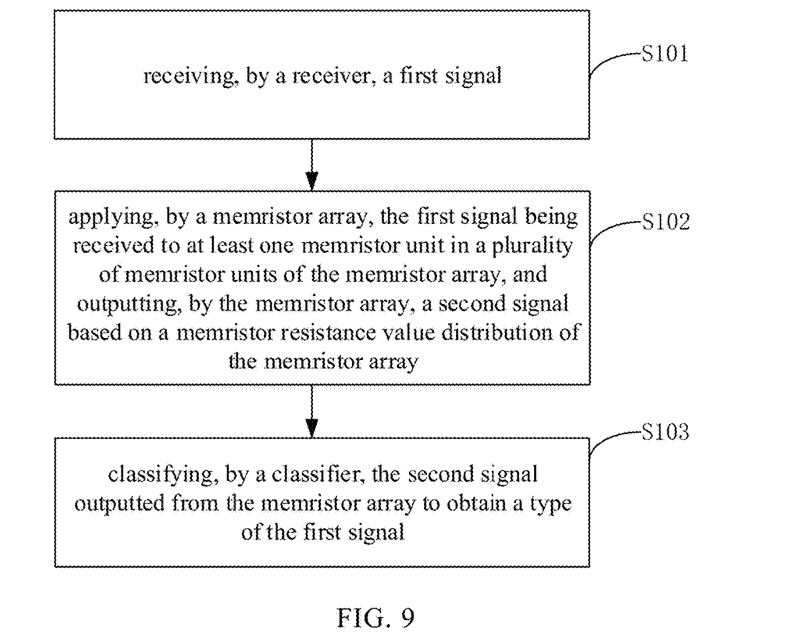
FIG. 9 is a flow chart of a signal processing method according to an exemplary embodiment of the present disclosure.

FIG. 9 is a flow chart of a signal processing method according to an exemplary embodiment of the present disclosure. For example, the signal processing method according to the embodiment of the present disclosure can be implemented by the above-described signal processing device.

Referring to FIG. 9, the signal processing method according to the exemplary embodiment of the present disclosure includes step S101 to step S103.

Step S101: receiving, by a receiver, a first signal. The first signal is a signal to be identified. For example, the first signal can be a non-stationary random signal. For example, the first signal can be an electroencephalogram signal. For example, the number of first signals may be one or more. That is to say, one first signal or a plurality of first signals can be identified to obtain a type(s) of the first signal(s) by using the signal processing method according to the exemplary embodiment of the present disclosure.

For example, before step S101, the signal processing method can further include: initializing a memristor array, so that initial states of respective memristors in the memristor array are substantially the same. For example, an initial state includes a high-resistance state and a low-resistance state. For example, a high-resistance state of a memristor may be 10 megohms (MΩ), and a low-resistance state of a memristor may be 50 kilo-ohms (KΩ).

Step S102: applying, by a memristor array, the first signal that has been received to at least one memristor unit in a plurality of memristor units of the memristor array, and outputting, by the memristor array, a second signal based on a memristor resistance value distribution of the memristor array, wherein the memristor unit includes a memristor. As a result, the memristor array can encode the first signal into the second signal based on the memristor resistance value distribution of the memristor array.

For example, in the signal processing method provided by the embodiment of the present disclosure, the memristor array further includes a plurality of word lines, a plurality of bit lines and a plurality of source lines; and the memristor unit further includes a transistor connected in series with the memristor in the memristor unit. Step S102 can further include: applying the first signal to a corresponding memristor unit through at least one bit line in the plurality of bit lines; and outputting the second signal through at least one source line in the plurality of source lines. For example, when the number of first signals that have been received is one, one bit line can be selected from the plurality of bit lines to apply the first signal to the corresponding memristor unit therethrough, and one corresponding source line can be selected from the plurality of source lines to output the second signal. For example, when the number of first signals that have been received is three, three bit lines can be selected from the plurality of bit lines to receive the three first signals, respectively, and corresponding source lines can be selected from the plurality of source lines to output second signals.

The embodiment in which the first signal is received through a bit line and the second signal is outputted through a source line is described above, but the present disclosure is not limited thereto. For example, as another example, step S102 can include: applying the first signal to a corresponding memristor unit through at least one source line in the plurality of source lines; and outputting the second signal through at least one bit line in the plurality of bit lines. For example, when the number of first signals that have been received is one, one source line can be selected from the plurality of source lines to receive the first signal, and a corresponding bit line can be selected from the plurality of bit lines to output the second signal. For example, when the number of first signals that have been received is three, three source lines can be selected from the plurality of source lines to receive the three first signals, respectively, and corresponding bit lines can be selected from the plurality of bit lines to output second signals.

For example, in the signal processing method provided by the embodiment of the present disclosure, the memristor array further includes a plurality of word lines, a plurality of bit lines and a plurality of source lines; and the memristor unit further includes a transistor connected in series with the memristor in the memristor unit. Step S102 can further include: segmenting the first signal that has been received to form signal segments, and applying respective signal segments to memristor units that correspond to source lines receiving the first signal among the memristor units in the memristor array, for example, different memristor units correspond to different segments of the first signal. After each memristor unit receives a corresponding segment of the first signal, a resistance value of the memristor in the memristor unit is changed under an action of the corresponding signal segment of the first signal. For example, a detailed method of segmenting the first signal can be referred to FIG. 4, FIG. 5 and corresponding description.

For example, in the signal processing method provided by the embodiment of the present disclosure, the memristor array further includes a plurality of word lines, a plurality of bit lines and a plurality of source lines; and the memristor unit further includes a transistor connected in series with the memristor in the memristor unit. Step S102 can further include: receiving a switch control signal through at least one word line in the plurality of word lines, and selecting a memristor unit to be applied with the first signal based on the switch control signal. For example, the switch control signal can include a set signal or a reset signal, for selecting a corresponding memristor or not selecting a corresponding memristor.

For example, before step S102, the signal processing method can further include: pre-processing, by a pre-processing circuit, the first signal that has been received, to form a pre-processed signal having an amplitude within a predetermined range. For example, the pre-processing includes at least one selected from the group consisting of amplifying the first signal that has been received and level shifting the first signal that has been received. For example, the predetermined range is a resistive voltage interval of the memristor or a read voltage interval of the memristor.

Step S103: classifying, by a classifier, the second signal outputted from the memristor array to obtain a type of the first signal. As described above, with respect to different first signals, different memristor resistance distributions of the memristor array can be obtained, so the second signal based on the memristor resistance distribution of the memristor array can be classified to obtain the type of the first signal.

For detailed contents of step S102 and step S103, corresponding description in the above-described signal processing device can be referred to, and details will not be repeated here.

For example, in step S103, the second signal outputted from the memristor array can be classified by a neural network classifier using a neural network classification method, to obtain the type of the first signal. For example, the neural network classification method can include a back propagation (BP) neural network method, a radial basis function (RBF) neural network method, a convolutional neural network method, etc., and may be selected according to needs.

For example, the signal processing method according to the embodiment of the present disclosure further includes training the neural network classifier with a training sample set to set parameters of the neural network classifier. For example, in a case where the first signal is an electroencephalogram signal and the type of the first signal includes a first-type electroencephalogram signal, a second-type electroencephalogram signal, and a third-type electroencephalogram signal, training samples can include: a plurality of first-type training samples obtained after processing a plurality of first-type electroencephalogram signals at least through step S101 and step S102; a plurality of second-type training samples obtained after processing a plurality of second-type electroencephalogram signals at least through step S101 and step S102; and a plurality of third-type training samples obtained after processing a plurality of third-type electroencephalogram signals at least through step S101 and step S102; and the plurality of first-type training samples, the plurality of second-type training samples and the plurality of third-type training samples as described above are combined to obtain the training sample set. The above is only a case in which the type of the first signal includes three different types, but the present disclosure is not limited thereto; cases in which the type of the first signal includes two or more different types can also be processed by using a similar method, and details will not be repeated here. In addition, it should be noted that, for a specific method of training the neural network classifier with the training sample set, the neural network classification methods in the prior art can be referred to, which is not be limited in the present disclosure.

It should be noted that, the step of training a classifier with training samples to set parameters of the classifier can be executed before step S101, can be executed before step S102, or can be executed before step S103.

What have been described above are only specific implementations of the present disclosure, and the protection scope of the present disclosure is not limited thereto. Any changes or substitutions easily occur to those skilled in the art within the technical scope of the present disclosure should be covered in the protection scope of the present disclosure. Therefore, the protection scope of the present disclosure should be determined based on the protection scope of the claims.

What is claimed is:

1. A signal processing device, comprising a receiver, a memristor array and a classifier, wherein the receiver is configured to receive a first signal;
   the memristor array comprises a plurality of memristor units, each of the plurality of memristor units comprises a memristor, and the memristor array is configured to apply the first signal that has been received to at least one memristor unit in the plurality of memristor units, such that at least one memristor unit in the plurality of memristor units encodes the first signal into a second signal, the second signal refers to a memristor resistance value distribution of the memristor array, and output the second signal based on the memristor resistance value distribution of the memristor array, wherein the second signal comprises at least one conductance variation ratio of at least one memristor, wherein each conductance variation ratio refers to a ratio of a difference between a conductance of a memristor after the first signal is applied and the conductance of the memristor before the first signal is applied to the conductance of the memristor before the first signal is applied; and
   the classifier is configured to classify the second signal based on the memristor resistance value distribution of the memristor array to obtain a type of the first signal, and the second signal is outputted from the memristor array.

2. The signal processing device according to claim 1, wherein the memristor array further comprises a plurality of word lines, a plurality of bit lines and a plurality of source lines; and
   each of the plurality of memristor units is correspondingly connected with one word line in the plurality of word lines, one bit line in the plurality of bit lines, and one source line in the plurality of source lines, respectively.

3. The signal processing device according to claim 2, wherein the memristor array is configured to:
   apply the first signal to at least one memristor unit in the plurality of memristor units through at least one bit line in the plurality of bit lines, and output the second signal through at least one source line in the plurality of source lines; or
   apply the first signal to at least one memristor unit in the plurality of memristor units through at least one source line in the plurality of source lines, and output the second signal through at least one bit line in the plurality of bit lines.

4. The signal processing device according to claim 2, wherein the memristor array is further configured to segment the first signal that has been received to form signal segments, and apply respective signal segments to corresponding memristor units in the plurality of memristor units.

5. The signal processing device according to claim 2, wherein the memristor array is configured to receive a switch control signal through at least one word line in the plurality of word lines, and select a memristor unit to be applied with the first signal based on the switch control signal.

6. The signal processing device according to claim 1, wherein each of the plurality of memristor units further comprises a transistor connected in series with the memristor in each of the plurality of memristor units.

7. The signal processing device according to claim 1, wherein the memristor in each of the plurality of memristor units is a continuously adjustable multi-resistance state memristor.

8. The signal processing device according to claim 1, further comprising a pre-processing circuit, wherein the pre-processing circuit is configured to pre-process the first signal received by the receiver, so as to form a pre-processed signal having an amplitude within a predetermined range.

9. The signal processing device according to claim 8, wherein the pre-processing circuit comprises at least one of an amplifying circuit and a level shift circuit.

10. The signal processing device according to claim 8, wherein the predetermined range is a resistive voltage interval of the memristor or a read voltage interval of the memristor.

11. The signal processing device according to claim 1, wherein the first signal received by the receiver is an electroencephalogram signal.

12. A signal processing method, comprising:
    receiving, by a receiver, a first signal;

applying, by a memristor array, the first signal that has been received to at least one memristor unit in a plurality of memristor units of the memristor array, such that at least one memristor unit in the plurality of memristor units encodes the first signal into a second signal, the second signal refers to a memristor resistance value distribution of the memristor array, and outputting, by the memristor array, a second signal based on a memristor resistance value distribution of the memristor array, wherein the memristor unit comprises a memristor, wherein the second signal comprises at least one conductance variation ratio of at least one memristor, wherein each conductance variation ratio refers to a ratio of a difference between a conductance of a memristor after the first signal is applied and the conductance of the memristor before the first signal is applied to the conductance of the memristor before the first signal is applied; and classifying, by a classifier, the second signal based on the memristor resistance value distribution of the memristor array to obtain a type of the first signal, and the second signal is outputted from the memristor array.

13. The signal processing method according to claim 12, wherein the memristor array further comprises a plurality of word lines, a plurality of bit lines and a plurality of source lines, the applying, by the memristor array, the first signal that has been received to at least one memristor unit in the plurality of memristor units of the memristor array, comprises:
applying the first signal to at least one memristor unit in the plurality of memristor units through at least one bit line in the plurality of bit lines, and
the outputting, by the memristor array, the second signal based on the memristor resistance value distribution of the memristor array, comprises:
outputting the second signal through at least one source line in the plurality of source lines.

14. The signal processing method according to claim 12, wherein the memristor array further comprises a plurality of word lines, a plurality of bit lines and a plurality of source lines, the applying, by the memristor array, the first signal that has been received to at least one memristor unit in the plurality of memristor units of the memristor array, comprises:
applying the first signal to at least one memristor unit in the plurality of memristor units through at least one source line in the plurality of source lines, and
the outputting, by the memristor array, the second signal based on the memristor resistance value distribution of the memristor array, comprises:
outputting the second signal through at least one bit line in the plurality of bit lines.

15. The signal processing method according to claim 12, wherein the applying, by the memristor array, the first signal that has been received to at least one memristor unit in the plurality of memristor units of the memristor array, comprises:
segmenting the first signal that has been received to form signal segments, and applying respective signal segments to corresponding memristor units in the plurality of memristor units.

16. The signal processing method according to claim 12, wherein the memristor array further comprises a plurality of word lines, a plurality of bit lines and a plurality of source lines, and the applying, by the memristor array, the first signal that has been received to at least one memristor unit in the plurality of memristor units of the memristor array, comprises:
receiving a switch control signal through at least one word line in the plurality of word lines, and selecting a memristor unit to be applied with the first signal based on the switch control signal.

17. The signal processing method according to claim 12, further comprising: pre-processing, by a pre-processing circuit, the first signal that has been received, so as to form a pre-processed signal having an amplitude within a predetermined range.

18. The signal processing method according to claim 17, wherein the pre-processing comprises at least one selected from the group consisting of amplifying the first signal that has been received and level shifting the first signal that has been received.

19. The signal processing method according to claim 17, wherein the predetermined range is a resistive voltage interval of the memristor or a read voltage interval of the memristor.

20. The signal processing method according to claim 12, before the applying, by the memristor array, the first signal that has been received to at least one memristor unit in the plurality of memristor units of the memristor array, further comprising:
initializing the memristor array, so that initial states of respective memristors in the memristor array are substantially the same.

* * * * *